United States Patent
Chen et al.

(10) Patent No.: US 7,935,727 B2
(45) Date of Patent: May 3, 2011

(54) CETP INHIBITORS

(75) Inventors: Yi-Heng Chen, Whippany, NJ (US); Zhijian Lu, Clinton, NJ (US); Peter J. Sinclair, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 30 days.

(21) Appl. No.: 12/083,183

(22) PCT Filed: Oct. 13, 2006

(86) PCT No.: PCT/US2006/040400
§ 371 (c)(1),
(2), (4) Date: Apr. 4, 2008

(87) PCT Pub. No.: WO2007/047591
PCT Pub. Date: Apr. 26, 2007

(65) Prior Publication Data
US 2009/0124689 A1  May 14, 2009

Related U.S. Application Data

(60) Provisional application No. 60/728,069, filed on Oct. 19, 2005.

(51) Int. Cl.
*A01N 47/10* (2006.01)
*A61K 31/27* (2006.01)
*C07C 331/00* (2006.01)
*C07C 381/00* (2006.01)
*C07C 333/00* (2006.01)
*C07C 261/00* (2006.01)
*C07C 269/00* (2006.01)
*C07C 271/00* (2006.01)

(52) U.S. Cl. ............ 514/477; 514/478; 558/1; 558/233; 558/234; 558/241; 560/27

(58) Field of Classification Search .................. 514/477, 514/478; 558/1, 233, 234, 241; 560/27
See application file for complete search history.

(56) References Cited

U.S. PATENT DOCUMENTS

| | | | |
|---|---|---|---|
| 5,599,952 | A | 2/1997 | Matsumoto et al. |
| 6,458,803 | B1 | 10/2002 | Sikorski et al. |
| 2004/0058903 | A1 | 3/2004 | Takasugi et al. |
| 2004/0082658 | A1 | 4/2004 | Harter et al. |
| 2004/0220231 | A1 | 11/2004 | Lee et al. |
| 2004/0229957 | A1 | 11/2004 | Shinkai et al. |

FOREIGN PATENT DOCUMENTS
WO  WO 2005/100298  10/2005

*Primary Examiner* — Shengjun Wang
*Assistant Examiner* — Sarah Pihonak
(74) *Attorney, Agent, or Firm* — Mark R. Daniel; James L. McGinnis

(57) ABSTRACT

Compounds having a biphenyl group substituted with a phenyl or heteroaromatic group, as shown in Formula I, including pharmaceutically acceptable salts of the compounds, are CETP inhibitors, and are useful for raising HDL-cholesterol, reducing LDL-cholesterol, and for treating or preventing atherosclerosis:

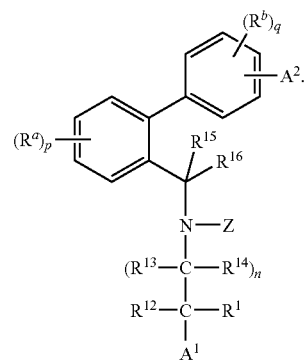

17 Claims, No Drawings

CETP INHIBITORS

CROSS REFERENCE TO RELATED APPLICATIONS

This application is a U.S. National Phase application under 35 U.S.C. §371 of PCT Application No. PCT/US2006/040400, filed Oct. 13, 2006, which claims priority under 35 U.S.C. §119(e) from U.S. application Ser. No. 60/728,069, filed Oct. 19, 2005.

FIELD OF THE INVENTION

This invention relates to a class of chemical compounds that inhibit cholesterol ester transfer protein (CETP) and therefore may have utility in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transferprotein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. New compounds are needed so that one or more pharmaceutical compounds can be found that are safe and effective. The novel compounds described herein are very potent CETP inhibitors. Structurally similar classes of CETP inhibiting compounds can be found in WO2005/100298 and WO2006/056854, both of which were published after the priority date of this application.

SUMMARY OF THE INVENTION

Compounds having Formula I, including pharmaceutically acceptable salts of the compounds, are CETP inhibitors, having the utilities described below:

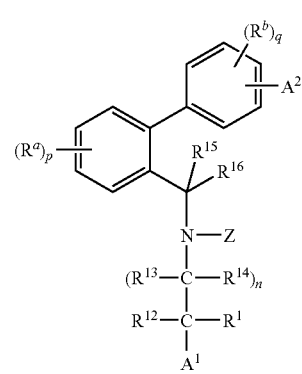

DETAILED DESCRIPTION OF THE INVENTION

In formula I, the phenyl ring that is substituted with $R^a$ groups may optionally have —N= in place of —(CH)= at one of the 4 positions that is open to substitution with $R^a$ in formula I;

$A^1$ is selected from the group consisting of:
(a) an aromatic ring selected from phenyl and naphthyl;
(b) a phenyl ring fused to a 5-7 membered non-aromatic cycloalkyl ring, which optionally comprises 1-2 double bonds;
(c) a 5-6-membered heterocyclic ring having 1-4 heteroatoms independently selected from N, S, and O, and optionally also comprising 1-3 double bonds and a carbonyl group or —N(O)— group, wherein the point of attachment of $A^1$ to the carbon atom to which $A^1$ is attached is a carbon atom of $A^1$;
(d) a benzoheterocyclic ring comprising a phenyl ring fused to a 5-6-membered heterocyclic ring having 1-3 heteroatoms independently selected from O, N, and S and optionally 1-2 double bonds, wherein the point of attachment of $A^1$ to the carbon atom to which $A^1$ is attached is a carbon atom of $A^1$; and
(e) a —$C_3$-$C_8$ cycloalkyl ring optionally having 1-3 double bonds;
wherein $A^1$ is optionally substituted with 1-5 substituent groups independently selected from $R^c$;

$A^2$ is selected from the group consisting of (a) phenyl which is optionally substituted with 1-5 substituents independently selected from $R^b$ and (b) a 5-6-membered heterocyclic ring having 1-4 heteroatoms independently selected from N, S, and O, and optionally also comprising 1-3 double bonds and a carbonyl group or —N(O)— group, wherein the point of attachment of the heterocyclic ring to the phenyl to which $A^2$ is attached is a carbon atom of the heterocyclic ring, wherein the heterocyclic ring is substituted with 1-2 groups independently selected from —$CO_2H$, —$CO_2C_1$-$C_6$alkyl, —C(=O)S$C_1$-$C_6$alkyl, —CN, —$NO_2$, —C(=O)H, —OH, —$C_2$-$C_6$ alkenyl, —$C_2$-$C_6$ alkynyl, —$OC_2$-$C_6$ alkenyl, —$OC_2$-$C_6$ alkynyl, —C(=O)$C_1$-$C_6$alkyl, —$NR^3R^4$, —C(=O)$NR^3R^4$, —$NR^3$C(=O)O$C_1$-$C_6$ alkyl, —$NR^3$C(=O)$NR^3R^4$, —S(O)$_x$$C_1$-$C_6$ alkyl, —S(O)$_y$$NR^3R^4$, —$NR^3$S(O)$_y$$NR^3R^4$, —$C_3$-$C_8$ cycloalkyl optionally having 1-3 double bonds, —O$C_3$-$C_8$ cycloalkyl optionally having 1-3 double bonds, and —C(=O)$C_3$-$C_8$ cycloalkyl, and is optionally also substituted with 1-3 groups independently selected from —$C_1$-$C_6$ alkyl, —O$C_1$-$C_6$alkyl, and halogen, wherein —$C_1$-$C_6$ alkyl, —$C_2$-$C_6$ alkenyl, —$C_2$-$C_6$ alkynyl, and —$C_3$-$C_8$ cycloalkyl optionally having 1-3 double bonds in all cases are optionally substituted with 1-15 halogens and I phenyl group which is optionally substituted with 1-5 substituent groups independently selected from halogen, —$CH_3$, —$CF_3$, —$OCH_3$, and —$OCF_3$;

Each $R^a$, $R^b$, and $R^c$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —O$C_1$-$C_6$alkyl, —O$C_2$-$C_6$ alkenyl, —O$C_2$-$C_6$ alkynyl, —O$C_3$-$C_9$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)S$C_1$-$C_6$alkyl, —OH, —$NR^3R^4$, —C(=O)$NR^3$,$R^4$, —$NR^3$C(=O)$_x$O$C_1$-$C_6$alkyl, —$NR^3$C(=O)$NR^3$,$R^4$, —S(O)$_x$$C_1$-$C_6$ alkyl, —S(O)$_y$$NR^3R^4$, —$NR^3$S(O)$_y$$NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$, $R^b$, or $R^c$ is attached is a carbon atom, wherein said heterocyclic ring is optionally substituted with 1-5 substituent groups independently selected from halogen, —$C_1$-$C_3$ alkyl, and —O$C_1$-$C_3$ alkyl, wherein —$C_1$-$C_3$ alkyl and —O$C_1$-$C_3$ alkyl are optionally substituted with 1-7 halogens;

wherein when $R^a$, $R^b$, and $R^c$ are selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —O$C_1$-$C_6$alkyl, —O$C_2$-$C_6$ alkenyl, —O$C_2$-$C_6$ alkynyl, —O$C_3$-$C_8$ cycloalkyl optionally having 1-3 double bonds, —C(=O)$C_1$-$C_6$alkyl, —C(=O)$C_3$-$C_9$ cycloalkyl, —$CO_2C_1$-$C_6$alkyl, —C(=O)S$C_1$-$C_6$alkyl, —$NR_3$C(=O)O$C_1$-$C_6$ alkyl, and —S(O)$_x$$C_1$-$C_6$ alkyl, then $R^a$, $R^b$, and $R^c$ are optionally substituted with 1-15 halogens and are optionally also substituted with 1-3 substituent groups independently selected from (a) —OH, (b) —CN, (c) —$NR^3R^4$, (d) —$C_3$-$C_8$ cycloalkyl optionally having 1-3 double bonds and optionally substituted with 1-15 halogens, (e) —O$C_1$-$C_4$alkyl optionally substituted with 1-9 halogens and optionally also substituted with 1-2 substituent groups independently selected from —O$C_1$-$C_2$ alkyl and phenyl, (f) —O$C_3$-$C_8$ cycloalkyl optionally having 1-3 double bonds and optionally substituted with 1-15 halogens, (g) —$CO_2$H, (h) —C(=O)$CH_3$, (i) —$CO_2C_1$-$C_4$alkyl which is optionally substituted with 1-9 halogens, and (j) phenyl which is optionally substituted with 1-3 groups independently selected from halogen, —$CH_3$, —$CF_3$, —$OCH_3$, and —$OCF_3$;

wherein 2 groups $R^a$ that are on adjacent carbon atoms of the phenyl or optional pyridinyl ring of Formula I may optionally be joined to form a bridging moiety selected from —$CH_2CH_2CH_2$—, —$CH_2CH_2CH_2CH_2$—, and —CH=CH—CH=CH—, thereby yielding a cyclopentyl, cyclohexyl, or phenyl ring fused to the phenyl ring or optional pyridinyl ring of Formula I, wherein said cyclopentyl, cyclohexyl, or phenyl ring that is fused to the phenyl or optional pyridinyl ring of Formula I is optionally substituted with 1-2 groups $R^a$, wherein these $R^a$ groups cannot be connected to form additional fused rings;

n is 0 or 1;
p is an integer from 0-4;
q is an integer from 0-4;
x is 0, 1, or 2;
y is 1 or 2;
Z is selected from the group consisting of —S(O)$_x$$C_1$-$C_6$ alkyl, —S(O)$_2$$NR^{17}R^{18}$, —C(=S)O$C_1$-$C_6$alkyl, and —C(=O)X, wherein X is selected from the group consisting of H, —$C_1$-$C_6$ alkyl, —O$C_1$-$C_6$ alkyl, —S$C_1$-$C_6$ alkyl, and —$NR^3$,$R^4$; wherein —$C_1$-$C_6$ alkyl in all instances is optionally substituted with 1-13 halogens and 1-2 substituents independently selected from —O$C_1$-$C_3$alkyl, —CN, and —$NO_2$, wherein —O$C_1$-$C_3$alkyl is optionally substituted with 1-7 halogens and is optionally also substituted with 1-2-O$C_1$-$C_2$ alkyl;

$R^1$, $R^{12}$, $R^{13}$, $R^{14}$, $R^{15}$, and $R^{16}$ are each independently selected from the group consisting of H, —OH, halogen, —$C_1$-$C_4$ alkyl, —$C_3$-$C_6$ cycloalkyl, —O$C_1$-$C_4$ alkyl, and —$NR^3R^4$, wherein —$C_1$-$C_4$ alkyl, —$C_3$-$C_6$ cycloalkyl, and —O$C_1$-$C_4$ alkyl are each optionally substituted with 1-9 halogens and are each optionally also substituted with 1-2 groups independently selected from —OH, —C(=O)$CH_3$, —OC(=O)$CH_3$, —O$C_1$-$C_2$ alkyl, and —O$C_1$-$C_2$ alkylene(O$C_1$-$C_2$alkyl), wherein either $R^1$ and $R^{12}$ together or $R^{13}$ and $R^{14}$ together may optionally form an oxo group;

$R^3$ and $R^4$ are each independently selected from H, —$C_1$-$C_5$ alkyl, —C(=O)$C_1$-$C_5$ alkyl and —S(O)$_y$$C_1$-$C_5$ alkyl, wherein —$C_1$-$C_5$ alkyl in all instances is optionally substituted with 1-11 halogens; and $R^{17}$ and $R^{18}$ are each independently selected from the group consisting of H, —$C_1$-$C_5$ alkyl, and —$C_3$-$C_7$ cycloalkyl, wherein —$C_1$-$C_5$ alkyl, and —$C_3$-$C_7$ cycloalkyl are optionally substituted with 1-13 halogens.

In the compounds described herein, alkyl groups are linear or branched, unless otherwise defined.

A subset of compounds described above or pharmaceutically acceptable salts thereof, have Formula Ia:

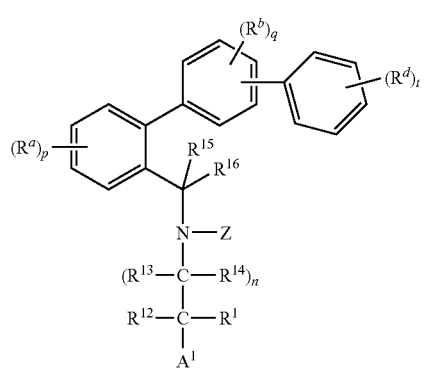

Ia

In these compounds the phenyl ring of formula Ia that is substituted with $R^a$ groups may optionally have —N= in place of —(CH)= at one of the 4 positions that is open to substitution with $R^a$ in formula Ia;

Each $R^d$ is independently selected from the group consisting of —$C_1$-$C_4$ alkyl, —$C_2$-$C_4$ alkenyl, cyclopropyl, —$OC_1$-$C_4$alkyl, —C(=O)$C_1$-$C_4$alkyl, —C(=O)H, —$CO_2$H, —$CO_2C_1$-$C_4$alkyl, —OH, —$NR^3R^4$, —$NR^3C$(=O)$OC_1$-$C_4$ alkyl, —S(O)$_xC_1$-$C_2$ alkyl, halogen, —CN, —$NO_2$, and a 5-6-membered heterocyclic ring having 1-2 heteroatoms independently selected from N, S, and O, wherein the point of attachment of said heterocyclic ring to the phenyl ring to which $R^d$ is attached is a carbon atom, wherein said heterocyclic ring is optionally substituted with 1-5 substituent groups independently selected from halogen;

wherein when $R^d$ is selected from the group consisting of —$C_1$-$C_4$ alkyl, —$C_2$-$C_4$ alkenyl, cyclopropyl, —$OC_1$-$C_4$alkyl, —C(=O)$C_1$-$C_4$alkyl, —$CO_2C_1$-$C_4$alkyl, —$NR^3C$(=O—O)$OC_1$-$C_4$ alkyl, and —S(O)$_xC_1$-$C_2$ alkyl, then the alkyl, alkenyl and cyclopropyl group of $R^d$ is optionally substituted with 1-5 halogens and is optionally substituted with one substituent group selected from (a) —OH, (b) —$NR^3R^4$, (c) —$OCH_3$ optionally substituted with 1-3 fluorine atoms and optionally substituted with one phenyl group, and (d) phenyl which is optionally substituted with 1-3 groups independently selected from halogen, —$CH_3$, —$CF_3$, —$OCH_3$, and —$OCF_3$; and t is an integer from 0-5.

A subset of the compounds described above has Formula Ib, including pharmaceutically acceptable salts.

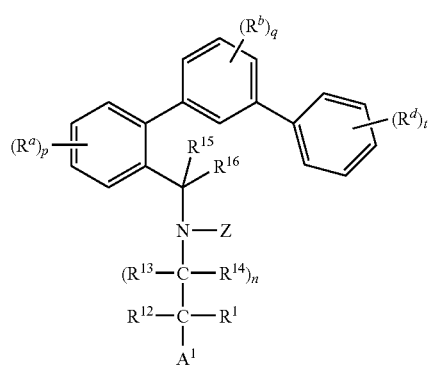

Ib

In the compounds of Formula Ib, the phenyl ring that is substituted with $R^a$ groups may optionally have —N= in place of —(CH)= at one of the 4 positions that is open to substitution with $R^a$ in formula Ib. Other groups are as defined previously.

In a subset of the compound of Formula I, or a pharmaceutically acceptable salt thereof, the phenyl ring of formula I that is substituted with $R^a$ groups may optionally have —N= in place of —(CH)= at one of the 4 positions that is open to substitution with $R^a$ in Formula I; and $A^2$ is a 5-6-membered heterocyclic ring having 1-4 heteroatoms independently selected from N, S, and O, and optionally also comprising 1-3 double bonds and a carbonyl group or —N(O)— group, wherein the point of attachment of the heterocyclic ring to the phenyl to which $A^2$ is attached is a carbon atom of the heterocyclic ring, wherein the heterocyclic ring is substituted with 1-2 groups independently selected from —$CO_2$H, —$CO_2C_1$-$C_6$alkyl, —C(=O)$SC_1$-$C_6$alkyl, —CN, —$NO_2$, —C(=O)H, —OH, —$C_2$-$C_6$ alkenyl, —$C_2$-$C_6$ alkynyl, —$OC_2$-$C_6$alkenyl, —$OC_2$-$C_6$alkynyl, —C(=O)$C_1$-$C_6$alkyl, —$NR^3R^4$, —C(=O)$NR^3R^4$, —$NR^3C$(=O)$OC_1$-$C_6$ alkyl, —$NR^3C$(=O)$NR^3R^4$, —S(O)$_xC_1$-$C_6$ alkyl, —S(O)$_yNR^3$, $R^4$, —$NR^3S$(O)$_yNR^3R^4$, —$C_3$-$C_8$ cycloalkyl optionally having 1-3 double bonds, —$OC_3$-$C_8$ cycloalkyl optionally having 1-3 double bonds, and —C(=O)$C_3$-$C_8$ cycloalkyl, and is optionally also substituted with 1-3 groups independently selected from of —$C_1$-$C_6$ alkyl, —$OC_1$-$C_6$alkyl, and halogen, wherein —$C_1$-$C_6$ alkyl, —$C_2$-$C_6$ alkenyl, —$C_2$-$C_6$ alkynyl, and —$C_3$-$C_8$ cycloalkyl optionally having 1-3 double bonds in all cases are optionally substituted with 1-15 halogens and 1 phenyl group which is optionally substituted with 1-5 substituents independently selected from halogen, —$CH_3$, —$CF_3$, —$OCH_3$, and —$OCF_3$.

In subsets of the compound of Formula I, $A^2$ is pyridyl or pyrimidinyl.

In subsets of the compounds described above, $A^1$ is selected from the group consisting of phenyl, naphthyl, —$C_3$-$C_6$ cycloalkyl, and a heterocyclic 5-6 membered ring having 1-3 heteroatoms independently selected from O, N, and S, and optionally also comprising 1-3 double bonds and a carbonyl group or —N(O)— group, wherein the point of attachment of $A^1$ to the carbon atom to which $A^1$ is attached is a carbon atom of $A^1$, wherein $A^1$ is optionally substituted with 1-2 substituent groups $R^c$, wherein each $R^c$ is independently selected from —$C_1$-$C_4$ alkyl, —$OC_1$-$C_3$ alkyl, —C(=O)$C_1$-$C_3$alkyl, —C(=O)H, —$NO_2$, —CN, —S(O)$_xC_1$-$C_3$ alkyl, —$NR^3R^4$, —$C_2$-$C_3$ alkenyl, —C(=O)$NR^3R^4$, halogen, —$C_3$-$C_6$ cycloalkyl, and a 5-6-membered heterocyclic ring having 1-3 heteroatoms independently selected from N, S, and O, and optionally also comprising 1-3 double bonds, wherein $C_1$-$C_3$ alkyl, $C_1$-$C_4$ alkyl, and $C_2$-$C_3$alkenyl in all instances are optionally substituted with 1-3 halogens, and —$C_3$-$C_6$ cycloalkyl and the 5-6-membered heterocyclic ring are optionally substituted with 1-3 substituents independently selected from halogen and —$C_1$-$C_3$ alkyl.

In subsets of the compounds described previously, each $R^a$ is independently selected from the group consisting of halogen, —$NR^3R^4$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —C(=O)$C_1$-$C_3$alkyl, —C(=O)$C_3$-$C_6$ cycloalkyl, —C(=O)H, —$CO_2$H, —$CO_2C_1$-$C_3$ alkyl, —C(=O)$NR^3R^4$, —CN, —$NO_2$, and a 5-6-membered heterocyclic ring having 1-4 heteroatoms independently selected from N, S, and O, and optionally 1-3 double bonds, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$;

wherein 2 groups $R^a$ that are on adjacent carbon atoms of the phenyl ring of Formula I, Ia or Ib that is substituted with $R^a$ may optionally be joined to form a bridging moiety selected from —$CH_2CH_2CH_2$—, —$CH_2CH_2CH_2CH_2$—, and —CH=CH—CH=CH—, thereby yielding a cyclopentyl, cyclohexyl, or phenyl ring fused to the phenyl ring of Formula I, Ia or Ib, wherein said cyclopentyl, cyclohexyl, or phenyl ring of Formula I, Ia or Ib is optionally substituted with 1-2 groups $R^a$;

n is an integer selected from 0 and 1;
p and q are each integers independently selected from 0-3;
t when present is an integer selected from 0-4;
x is an integer selected from 0, 1, and 2; and
y is an integer selected from 1 and 2.

In subsets of the compounds described above, $R^1$ is selected from the group consisting of H, F, OH, $C_1$-$C_3$ alkyl, and —$OC_1$-$C_3$ alkyl, wherein $C_1$-$C_3$ alkyl and —$OC_1$-$C_3$ alkyl are each optionally substituted with 1-3 halogens and also are optionally substituted with one —$OC_1$-$C_2$alkyl.

In subsets of the compounds described above, $R^3$ and $R^4$ are each independently selected from H and —$C_1$-$C_3$ alkyl.

In subsets of the compounds described above, $R^{12}$, $R^{13}$, $R^{14}$, $R^{15}$, and $R^{16}$ are each H or —$C_1$-$C_3$ alkyl.

In subsets of the compounds described above, Z is selected from the group consisting of —C(=O)$C_1$-$C_3$ alkyl, —C(=O)O$C_1$-$C_3$ alkyl, —S(O)$_y$$C_1$-$C_3$ alkyl, —C(=O)H, —C(=O)NR$^3$R$^4$, —C(=O)S$C_1$-$C_3$ alkyl, and —C(=S) O$C_1$-$C_3$ alkyl.

In subsets of the compounds of Formula I, Ia, or Ib, $A^1$ is selected from the group consisting of phenyl, thienyl, furyl, pyridyl, 1-oxidopyridinyl, quinolyl, isoquinolyl, benzofuranyl, dihydrobenzofuranyl, indolyl, dihydroindolyl, oxazolyl, isoxazolyl, oxadiazolyl, and $C_3$-$C_6$ cycloalkyl.

In subsets of the compounds of Formula I, Ia, or Ib, $R^1$ is H or $CH_3$;
$R^{12}$, $R^{13}$, $R^{14}$, $R^{15}$, and $R^{16}$ are each H; and
n is 0. In other subsets, $R^1$ is H.

In subsets of the compounds above, $A^1$ is phenyl.

In subsets of the compounds of Formula Ia or Ib, $R^d$ is selected from the group consisting of halogen, —$C_1$-$C_3$ alkyl, —$C_2$-$C_3$ alkenyl, —$OC_1$-$C_3$ alkyl, —NR$^3$R$^4$, —CO$_2$H, —CO$_2$$C_1$-$C_3$ alkyl, and —CN, wherein —$C_1$-$C_3$ alkyl and —$C_2$-$C_3$ alkenyl in all uses are optionally substituted with 1-3 halogens and optionally one —OH group; and
t is an integer from 0-3.

In subsets of the compounds described above, $R^a$, $R^b$ and $R^c$ are each independently selected from the group consisting of halogen, —NR$^3$R$^4$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —C(=O)$C_1$-$C_3$alkyl, —C(=O)$C_3$-$C_6$ cycloalkyl, —C(=O)H, —CO$_2$H, —CO$_2$$C_1$-$C_3$alkyl, —C(=O)NR$^3$R$^4$, —CN, —NO$_2$, and a 5-6-membered heterocyclic ring having 1-4 heteroatoms independently selected from N, S, and O, and optionally 1-3 double bonds, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$.

In subsets of the compounds described above, $R^a$, $R^b$ and $R^c$ are each independently selected from the group consisting of halogen, cyclopropyl, —NR$^3$R$^4$, —$C_1$-$C_3$ alkyl, —$C_2$-$C_3$ alkenyl, —$OC_1$-$C_3$ alkyl, —CN, —NO$_2$, and pyridinyl, wherein cyclopropyl, $C_1$-$C_3$ alkyl and $C_2$-$C_3$ alkenyl in all instances are optionally substituted with 1-3 halogens, and pyridinyl is optionally substituted with 1-3 substituents independently selected from the group consisting of halogen, —$CH_3$, —$CF_3$, —$OCH_3$, and —$OCF_3$.

In subsets of the compounds described above, $R^a$, $R^b$ and $R^c$ are each independently selected from the group consisting of halogen, —NR$^3$R$^4$, —$C_1$-$C_3$ alkyl, —$C_2$-$C_3$ alkenyl, —$OC_1$-$C_3$ alkyl, —CN, —NO$_2$, and pyridinyl, wherein $C_1$-$C_3$ alkyl and $C_2$-$C_3$ alkenyl in all instances is optionally substituted with 1-3 halogens, and pyridinyl is optionally substituted with 1-3 substituents independently selected from the group consisting of halogen, —$CH_3$, —$CF_3$, —$OCH_3$, and —$OCF_3$, or a pharmaceutically acceptable salt thereof.

In embodiments of the compounds of Formula I, Ia, Ib, and Ic, including pharmaceutically acceptable salts thereof, 2 groups $R^a$ that are on adjacent carbon atoms of the phenyl or optional pyridinyl ring of Formula I, Ia or Ib do not have the option of joining to form a bridging moiety selected from —$CH_2CH_2CH_2$—, —$CH_2CH_2CH_2CH_2$—, and —CH=CH—CH=CH— to yield a cyclopentyl, cyclohexyl, or phenyl ring fused to the phenyl ring or optional pyridinyl ring of Formula I, Ia or Ib.

In subsets of the compounds of formula I, Ia and Ib, including pharmaceutically acceptable salts thereof, the phenyl ring of formula I, Ia and Ib that is substituted with $R^a$ does not have the option of having —N= in place of one —CH= of the phenyl ring.

In general, the compounds of the invention have at least one substituent other than H on at least two of the four rings ($A^1$, $A^2$, the phenyl ring which is optionally a pyridine ring and has $R^a$ substituents, and the other phenyl ring). Often the compounds have at least one substituent on three of the four rings. Many embodiments have at least one substituent on all four of the rings in formula I, Ia and Ib. In many embodiments, the ring $A^2$ has 0-3 substituents, or has 1-3 substituents, or has 2-3 substituents. When $A^2$ is a heterocycle, $A^2$ has at least one substituent (e.g. 1-4 substituents, 1-3 substituents, or 2-3 substituents). The ring $A^1$ often has 0-3 substituents, or 1-3 substituents, or 2-3 substituents, or 2 substituents. The integers p and q are each independently in various embodiments 0-4, 0-3, 0-2, 1-3, 2-3, 2-4, or 1-2.

Definitions

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated. The term also includes a cycloalkyl ring fused to an aryl group. Examples of cycloalkyl include cyclopropyl, cyclopentyl, cyclohexyl, cycloheptyl, and the like. "Cycloalkyl" may also be defined to have one or more double bonds, such as cyclohexenyl or cyclohexadienyl, but cannot have the number of double bonds that would make the cycloalkyl group aromatic.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"Heterocyclyl," "heterocycle," and "heterocyclic" means a fully or partially saturated or aromatic 5-6 membered ring containing 1-4 heteroatoms independently selected from N, S and O, unless otherwise stated. A heterocycle which is aromatic is also known as heteroaromatic or heteroaryl.

"Benzoheterocycle" represents a phenyl ring fused to a 5-6-membered heterocyclic ring having 1-2 heteroatoms, each of which is O, N, or S, where the heterocyclic ring may be saturated or unsaturated, including aromatic. Examples include indole, benzofuran, 2,3-dihydrobenzofuran and quinoline.

"Halogen" includes fluorine, chlorine, bromine and iodine.

"Me" represents methyl.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to include all such isomeric forms of the compounds of Formula I and all mixtures of the compounds. When structures are shown with a stereochemical representation, other stereochemical structures are also included within the scope of this disclosure individually and collectively, such as enantiomers, diastereoisomers (where diastereomers are possible), and mixtures of the enantiomers and/or diastereomers, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites-Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are expected to be particularly effective in raising HDL-C and/or increasing the ratio of HDL-C to LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other thereapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerostic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149; 0) glucagon receptor antagonists;

(k) GLP-1; GLP-1 derivatives; GLP-1 analogs, such as exendins, such as for example exenatide (Byetta); and non-peptidyl GLP-1 receptor agonists;

(l) GIP-1;

(m) Non-sulfonylurea insulin secretagogues, such as the meglitinides (e.g. nateglinide and rapeglinide);

(n) GPR40 agonists;

(o) GPR119 agonists;

(p) GPR120 agonists; and (q) glucokinase activators.

These other active ingredients that may be used in combination with the current invention also include antiobesity compounds, including 5-HT(serotonin) inhibitors, neuropeptide Y5 (NPY5) inhibitors, melanocortin 4 receptor (Mc4r) agonists, cannabinoid receptor 1 (CB-1) antagonists/inverse agonists, and $β_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2)angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081x, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor ($MCH_2R$) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMv-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, aminone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14] Bn(6-14) and [D-Phe6,Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and $C_{75}$; (38) DGAT1 (diacylglycerol acyltransferase 1) inhibitors; (39) DGAT2 (diacylglycerol acyltransferase 2) inhibitors; (40) $ACC_2$ (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine; (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) a minorex; (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor. See Epps et al. (1995) *Method for measuring the activities of cholesteryl ester transfer protein (lipid transfer protein)*, Chem. Phys. Lipids. 77, 51-63.

Particles used in the assay were created from the following sources: Synthetic donor HDL particles containing DOPC (Dioleoyl Phosphatidyl Choline), BODIPY®-CE (Molecular Probes C-3927), triolein (a triglyceride), and apoHDL were essentially created by probe sonication as described by Epps et al, but with the addition of a non-diffusable quencher molecule, dabcyl dicetylamide, in order to reduce background fluorescence. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), and half the final concentration of acceptor particles was prepared, and 100 μL of the assay cocktail was added to each well of the plate. Test compounds in DMSO were added in a volume of 3 μL. The plate was mixed on a plate shaker and then incubated at 25° C. for 1 hour. A second assay cocktail containing donor particles, the remaining acceptor particles and 1×CETP buffer was prepared. 47 μL of the second assay cocktail was added to the reaction wells to start the assay. Assays were performed at 25° C. in a final volume of 150 μL. Final concentrations of materials were: 5 ng/μL donor particles, 30 ng/μL acceptor particles (each expressed by protein content), 1×CETP buffer, 0.8 nM recombinant human CETP (expressed in CHO cells and partially purified), and up to 2% DMSO when testing compounds. The assay was followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well.

Data was evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and example are provided so that the invention will be more fully appreciated and understood. Starting materials are made using known procedures or as shown below. Some of the intermediates were made or can be made using the methods disclosed in published PCT application WO2005/100298.

The examples should not be construed as limiting the invention in any way. The scope of the invention is defined by the appended claims. Compounds that inhibit CETP have an $IC_{50}$ value as measured using the assay described above of less than or equal to 50 μM. Compounds described as examples (Examples 1-4, 1A, and 4A) have an $IC_{50}$ value as measured using the assay described above in the range of about 29 nM-3500 nM.

Examples 1 and 1A

Step A

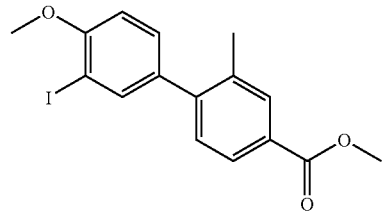

Methyl 3'-iodo-4'-methoxy-2-methylbiphenyl-4-carboxylate

Methyl 4'-methoxy-2-methylbiphenyl-4-carboxylate (1.2 g, 4.68 mmol), methanol (20 mL), ethyl acetate (5 mL), iodine (1.19 g, 4.68 mmol), and silver sulfate (1.46 g, 4.68 mmol) were stirred at room temperature for 2 hours to complete the reaction. Volatiles were removed under reduced pressure to afford a yellow solid. The resulting solid was treated with brine followed by ethyl acetate extractions. The combined extracts were dried over $Na_2SO_4$ followed by filtration and concentration to afford a purple oil. The resulting oil was purified on $SiO_2$ (Biotage HorizonFlash system, 40+M cartridge) to afford a white powder as the desired methyl 3'-iodo-4'-methoxy-2-methylbiphenyl-4-carboxylate. LCMS calc.=382.01; found=383.15 (M+1)+.

Step B

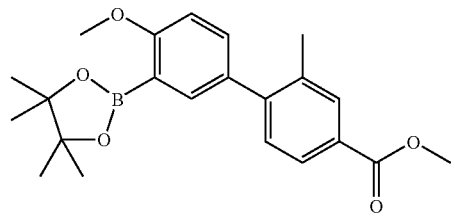

Methyl 4'-methoxy-2-methyl-3'-(4,4,5,5-tetramethyl-1,3,2-dioxaborolan-2-yl)biphenyl-4-carboxylate Methyl 3'-iodo-4'-methoxy-2-methylbiphenyl-4-carboxylate (500 mg, 1.308 mmol), bis(pinacolato)diboron (353 mg, 1.57 mmol), 1,1'-bis(diphenylphosphino)ferrocene-palladium dichloride dichloromethane adduct (214 mg, 0.262 mmol), potassium acetate (257 mg, 2.616 mmol) and 1,4-dioxane (2.5 mL) were sealed in a microwave vessel. The reaction mixture was irradiated by microwave at 140° C. for 20 minutes, then at 130° C. for 30 minutes. The reaction crude was treated with brine followed by ethyl acetate extractions. The combined extracts were dried over $Na_2SO_4$ followed by filtration and concentration in vacuo to afford a dark oil as the crude mixture of methyl 4'-methoxy-2-methyl-3'-(4,4,5,5-tetramethyl-1,3,2-dioxaborolan-2-yl)biphenyl-4-carboxylate, which was used without further purification for the next coupling. LCMS calc.=382.20; found=383.41 (M+1)+.

Example 1A

Step C

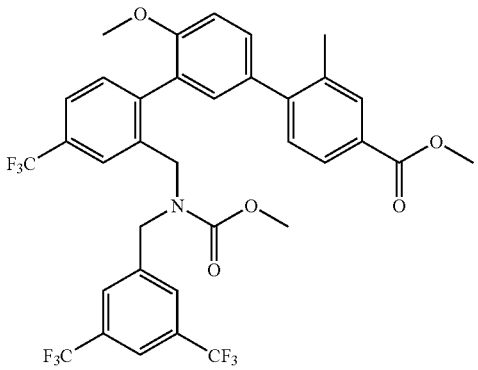

Methyl 2"-{[[3,5-bis(trifluoromethyl)benzyl](methoxycarbonyl)amino]methyl}-4'-methoxy-2-methyl-4"-(trifluoromethyl)-1,1':3',1"-terphenyl-4-carboxylate Methyl[3,5-bis(trifluoromethyl)benzyl][2-iodo-5-(trifluoromethyl)benzyl]carbamate (200 mg, 0.342 mmol), made using published methods, methyl 4'-methoxy-2-methyl-3'-(4,4,5,5-tetramethyl-1,3,2-dioxaborolan-2-yl)biphenyl-4-carboxylate (157 mg, 0.41 mmol), palladium (II) acetate (16 mg, 0.071 mmol), potassium carbonate (aqueous solution, 1M, 684 µL, 0.684 mmol) and acetone (1 mL) were combined and stirred in an 85° C. oil bath for 42 minutes to complete the reaction. The crude reaction mixture was cooled (ice bath) and dried ($Na_2SO_4$). The resulting dark mixture was purified on $SiO_2$ to afford a clear glass comprising methyl 2"-{[[3,5-bis(trifluoromethyl)benzyl](methoxycarbonyl)amino]methyl}-4'-methoxy-2-methyl-4"-(trifluoromethyl)-1,1':3',1"-terphenyl-4-carboxylate. LCMS calc.=713.18; found=714.30 $(M+1)^+$.

Example 1

Step D

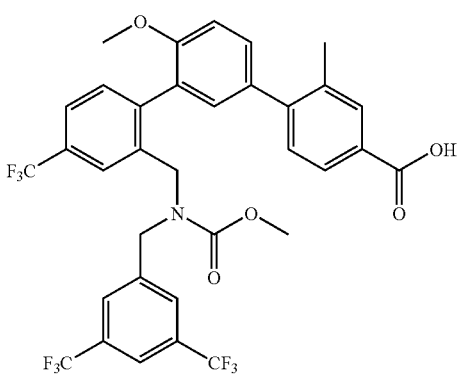

2"-{[[3,5-bis(trifluoromethyl)benzyl](methoxycarbonyl)amino]methyl}-4'-methoxy-2-methyl-4"-(trifluoromethyl)-1,1':3',1"-terphenyl-4-carboxylic acid Methyl 2"-{[[3,5-bis(trifluoromethyl)benzyl] (methoxycarbonyl)amino]methyl}-4'-methoxy-2-methyl-4"-(trifluoromethyl)-1,1':3',1"-terphenyl-4-carboxylate (34.7 mg, 0.0486 mmol), lithium hydroxide monohydrate (10 mg, 0.238 mmol), water (0.4 mL) and 1,4-dioxane (1 mL) were stirred at room temperature for 5.5 hours to complete the reaction. Crude mixture was acidified with HCl (aq, 1N, 6 mL). The resulting mixture was worked up with brine and extracted with ethyl acetate. The combined extracts were back-washed with water. The resulting organic layer was dried over $Na_2SO_4$, filtered and evaporated in vacuo to afford a clear oil. The resulting oil was purified on $SiO_2$ to afford as a clear glass 2"-{[[3,5-bis(trifluoromethyl)benzyl] (methoxycarbonyl)amino]methyl}-4'-methoxy-2-methyl-4"-(trifluoromethyl)-1,1':3',1"-terphenyl-4-carboxylic acid. LCMS calc.=699.17; found=700.29 $(M+1)^+$. $^1$H NMR ($CDCl_3$, 500 MHz) δ 8.01 (s, 1H), 7.95 (d, J=7.5 Hz, 1H), 7.72 (s, 1H), 7.58 (d, J=8.0 Hz, 1H), 7.55-7.46 (m, 1.5H), 7.43-7.34 (m, 2.5H), 7.32-7.25 (m, 1H), 7.07-7.5 (m, 1H), 4.62-4.22 (m, 4H), 3.77 (s, 3H), 3.73 (d, J=17 Hz, 3H), 3.32 (s, 3H).

Example 2

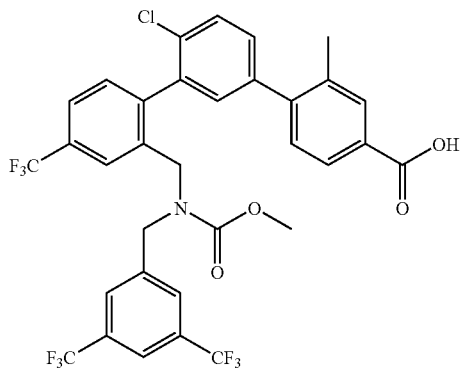

Step A

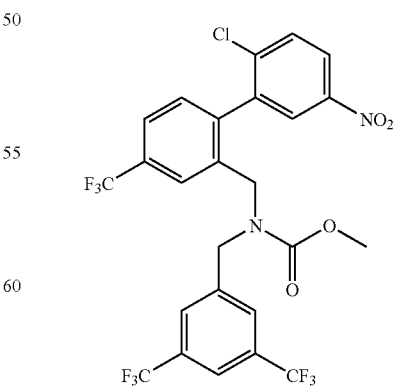

2-Chloro-5-nitro-phenyl boronic acid (0.613 g, 3.04 mmol), made using published methods, was added to a stirred mixture of methyl[3,5-bis(trifluoromethyl)benzyl][2-iodo-5-(trifluoromethyl)benzyl]carbamate (0.89 g, 1.521 mmol), tetrakis(triphenylphosphine) palladium (0.351 g, 0.304 mmol), and sodium carbonate (0.645 g, 6.08 mmol) in a mixture of aqueous ethanol (4.00 ml) and toluene (8.00 ml). The mixture was stirred under reflux for 2 h. The mixture was cooled, and the solvents were removed. Water was added and the mixture was extracted with dichloromethane (3×10 mL). The combined organic fractions were washed with brine (10 mL), dried over Na$_2$SO$_4$, filtered and the solvent was evaporated under reduced pressure. The residue was purified by column chromatography on silica gel Biotage 40M, eluting with CH$_2$Cl$_2$/hexane to give the product as a yellow solid. $^1$H NMR (CDCl$_3$, 500 MHz) δ 8.25 (dd, J=9, 2.5 Hz, 1H), 8.06 (s, 1H), 7.79 (s, 1H), 7.70 (t, J=9.0 Hz, 1H), 7.60-7.46 (m, 3H), 7.36 (d, J=8.0 Hz, 1H), 7.07-7.5 (m, 1H), 4.62-4.22 (m, 4H), 3.70 (s, 3H).

Step B

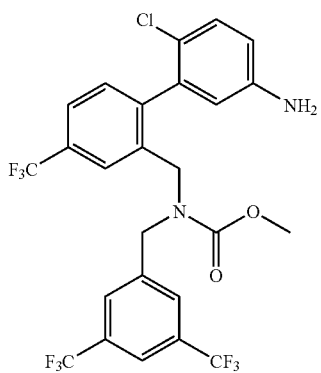

The title compound from Step A was charged with hydrogen at 1 atm with a catalytic amount of 1% Pt with V in MeOH. The mixture was stirred at room temperature for 1 h. TLC and LC/MS showed the reaction was complete. The mixture was filtered through Celite and the filtrate was evaporated under reduced pressure to give the title compound as a colorless solid. The residue was purified by column chromatography on silica gel Biotage 40M, eluting with EtOAc/isohexane (3:7) to give the title compound as a colorless solid. $^1$H NMR (CDCl$_3$, 500 MHz) δ 7.76 (s, 1H), 7.60 (d, J=8.0 Hz, 1H), 7.57 (m, 1H), 7.49 (m, 2H), 7.32 (d, J=7.5 Hz, 1H), 7.21 (m, 1H), 6.65 (m, 1H), 6.41 (s, 1H), 4.60-4.22 (m, 4H), 3.70 (m, 3H). LC-MS (M+1): 585.05.

Step C

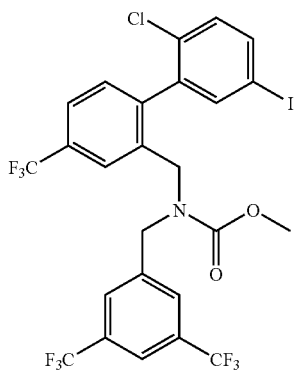

A solution of the title compound from Step B (300 mg, 0.513 mmol) in chloroform (20 ml) was added to a stirred, cooled 0° C. mixture of n-amyl nitrite (1.5 eq) and iodine (1.3 eq) in chloroform (10 ml), and the mixture was stirred at 80° C. for 1 h. TLC showed no starting material left. The purple mixture was cooled to room temperature and washed with a saturated solution of sodium thiosulfate and brine. The solvent was evaporated under reduced pressure. The residue was purified by column chromatography on silica gel Biotage 40M, eluting with EtOAc/isohexane (1:9) to give the title compound as a yellow solid. $^1$H NMR (CDCl$_3$, 500 MHz) δ 7.79 (s, 1H), 7.68 (m, 1H), 7.64 (d, J=8.0 Hz, 1H), 7.58 (m, 1H), 7.49 (m, 3H), 7.32 (d, J=8.0 Hz, 1H), 7.22 (d, J=8.0 Hz, 1H), 4.60-4.22 (m, 4H), 3.80 (m, 3H).

Step D

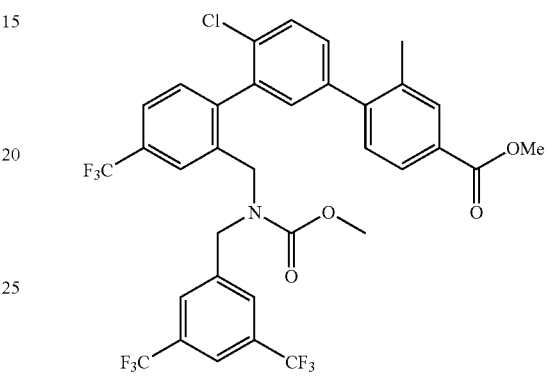

2-Methyl-4-(methoxycarbonyl)phenyl borate (73.8 mg, 0.267 mmol), which was made using published methods, was added to a stirred mixture of the title compound from Step C (93 mg, 0.134 mmol), tetrakis(triphenylphosphine) palladium (30.9 mg, 0.027 mmol), and sodium carbonate (31.2 mg, 0.294 mmol) in a mixture of aqueous ethanol (4.00 ml) and toluene (8.00 ml). The mixture was stirred under reflux for 2 h. The mixture was cooled, and the solvents were removed. Water was added and the mixture was extracted with dichloromethane (3×10 mL). The combined organic fractions were washed with brine (10 mL), dried over Na$_2$SO$_4$, filtered, and the solvent was evaporated under reduced pressure. The residue was purified by column chromatography on silica gel Biotage 40S, eluting with CH$_2$Cl$_2$/hexane (6:4) to give the title compound as a yellow solid. $^1$H NMR (CDCl$_3$, 500 MHz) δ 7.97 (s, 1H), 7.90 (d, J=8.0 Hz, 1H), 7.76 (s, 1H), 7.66 (d, J=7.5 Hz, 1H), 7.57 (m, 3H), 7.49 (m, 1H), 7.40 (d, J=8.5 Hz, 1H), 7.33 (m, 1H), 7.24 (d, J=8.5 Hz, 1H), 7.12 (s, 1H), 4.70-4.50 (m, 2H), 4.37-4.28 (m, 2H), 3.98 (s, 3H), 3.80 (m, 3H), 2.28 (s, 3H). LC-MS (M+): 718.37.

Step E

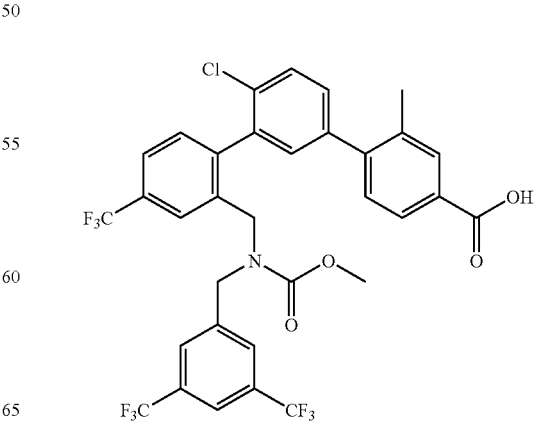

A mixture of the title compound from Step D (75 mg, 0.104 mmol), LiOH (1.04 mmol, 1M aqueous solution) in dioxane (2 ml) was stirred at room temperature for 24 h. The solvent was removed under vacuum. 1N HCl was added to adjust to pH ~4. The mixture was extracted with EtOAc (3×10 ml). The combined EtOAc layers were washed with brine and dried over sodium sulfate. The residue was purified by column chromatography on silica gel Biotage 40S, eluting with EtOAc/hexane (7:3) to give the title compound as a colorless solid. $^1$H NMR (CDCl$_3$, 500 MHz) δ 8.03 (s, 1H), 7.97 (d, J=8.5 Hz, 1H), 7.76 (s, 1H), 7.66 (d, J=8.5 Hz, 1H), 7.58 (m, 3H), 7.49 (m, 1H), 7.41 (d, J=8.0 Hz, 1H), 7.37 (m, 1H), 7.28 (m, 1H), 7.13 (s, 1H), 4.70-4.50 (m, 2H), 4.30-4.25 (m, 2H), 3.80 (m, 3H), 2.25 (s, 3H). LC-MS (M+1): 704.3.

Example 3

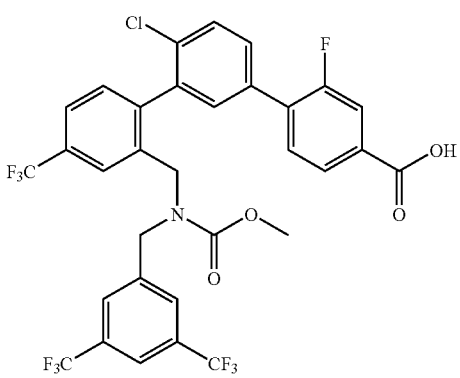

Step A

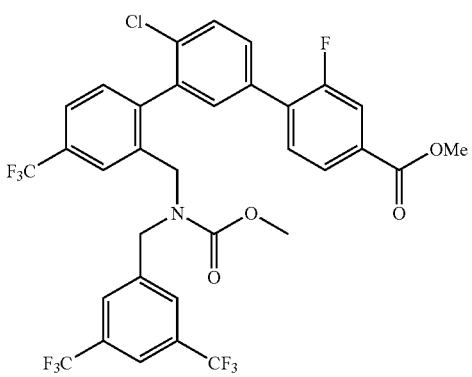

2-Fluoro-4-(methoxycarbonyl)phenyl boronic acid (52.9 mg, 0.267 mmol) was added to a stirred mixture of the title compound from Step C, Example 2 (93 mg, 0.134 mmol), tetrakis(triphenylphosphine) palladium (30.9 mg, 0.027 mmol), and sodium carbonate (31.2 mg, 0.294 mmol) in a mixture of aqueous ethanol (4.00 ml) and toluene (8.00 ml). The mixture was stirred under reflux for 2 h. The mixture was cooled, and the solvents were removed. Water was added, and the mixture was extracted with dichloromethane (3×10 mL). The combined organic fractions were washed with brine (10 mL), dried over Na$_2$SO$_4$, filtered, and the solvent was evaporated under reduced pressure. The residue was purified by column chromatography on silica gel Biotage 40S, eluting with CH$_2$Cl$_2$/hexane (6:4) to give the title compound as a yellow solid. $^1$H NMR (CDCl$_3$, 500 MHz) δ 7.91 (d, J=8.0 Hz, 1H), 7.83 (d, J=11.0 Hz, 1H), 7.74 (s, 1H), 7.66 (d, J=8.0 Hz, 1H), 7.58 (m, 4H), 7.48 (t, J=8.0 Hz, 2H), 7.40 (d, J=8.5 Hz, 1H), 7.39 (s, 1H), 4.60-4.30 (m, 4H), 3.98 (s, 3H), 3.77 (m, 3H). LC-MS (M+1): 722.36.

Step B

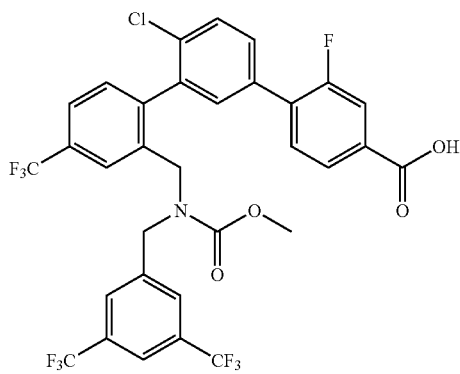

A mixture of the title compound from Step A (79 mg, 0.109 mmol), LiOH (1.09 mmol, 1M aqueous solution) in dioxane (2 ml) was stirred at room temperature for 6 h. The solvent was removed under vacuum. 1N HCl was added to adjust to pH ~4. The mixture was extracted with EtOAc (3×10 ml). The combined EtOAc layers were washed with brine and dried over sodium sulfate. The residue was purified by column chromatography on silica gel Biotage 40S, eluting with EtOAc/hexane (7:3) to give the title compound as a colorless solid. $^1$H NMR (CDCl$_3$, 500 MHz) δ 7.97 (d, J=8.5 Hz, 1H), 7.88 (d, J=11.0 Hz, 1H), 7.74 (s, 1H), 7.67 (d, J=8.5 Hz, 1H), 7.58 (m, 4H), 7.52 (t, J=8.0 Hz, 2H), 7.41 (d, J=8.0 Hz, 1H), 7.40 (s, 1H), 4.60-4.30 (m, 4H), 3.77 (m, 3H).

Examples 4 and 4A

Step A

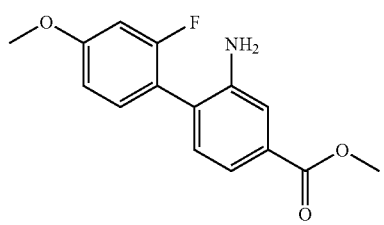

Methyl 2-amino-2'-fluoro-4'-methoxybiphenyl-4-carboxylate

1-Bromo-2-fluoro-4-methoxybenzene (750 mg, 3.66 mmol), [2-amino-4-(methoxycarbonyl)phenyl]boronic acid (856 mg, 4.39 mmol), potassium acetate (3.66 mL, 2M aq, 7.32 mmol), 1,1'-bis(diphenylphosphino)ferrocene-palladium dichloride dichloromethane adduct (299 mg, 10 mol. %) and ethanol (30 ml) were heated in an 80° C. oil bath for 3 hours. Reaction crude was worked up with brine, extracted with ethyl acetate, dried over Na$_2$SO$_4$, filtered and evaporated to afford a dark oil. This oil was purified by SiO$_2$ (Biotage HorizonFlash system, 40+M cartridge, 0-25% EtOAc/hexanes, v/v) to afford the title compound as a yellow crystalline solid. LCMS calc.=275.10; found=276.09 (M+1)$^+$.

Step B

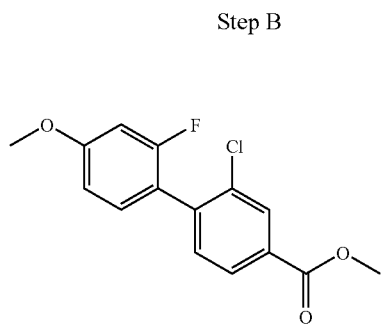

Methyl 2-chloro-2'-fluoro-4'-methoxybiphenyl-4-carboxylate

Amyl nitrite (420 μL, 3.19 mmol) and copper (II) chloride (343 mg, 2.55 mmol) were suspended in acetonitrile (5 mL) and heated in a 65° C. oil bath. To this hot mixture was added methyl 2-amino-2'-fluoro-4'-methoxybiphenyl-4-carboxylate (585 mg, 2.13 mmol, in 5 mL MeCN) in about 1 minute. The resulting mixture was heated in a 65° C. oil bath for a total time of 2 hours. The crude reaction mixture was purified on SiO$_2$ (Biotage HorizonFlash system, 40+M cartridge, 0-20% EtOAc/hexanes, v/v) to afford the title compound as a yellow oil. LCMS calc.=294.05; found=295.03 (M+1)$^+$.

Step C

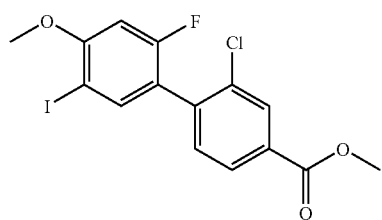

Methyl 2-chloro-2'-fluoro-5'-iodo-4'-methoxybiphenyl-4-carboxylate

Methyl 2-chloro-2'-fluoro-4'-methoxybiphenyl-4-carboxylate (550 mg, 1.87 mmol), methanol (8 mL), iodine (474 mg, 1.87 mmol), and silver sulfate (583 mg, 1.87 mmol) were stirred at room temperature for 2 hours to complete the reaction. The crude reaction mixture was worked up with NaHSO$_3$ (aq). Volatiles were removed under reduced pressure. The pot residue was worked up with brine, extracted with ethyl acetate, dried over Na$_2$SO$_4$, filtered and evaporated to afford a light brown solid. This solid was purified on SiO$_2$ (Biotage HorizonFlash system, 40+M cartridge, 0-20% EtOAc/hexanes, v/v) to afford the title compounds as a light yellow solid. LCMS calc.=419.94; found=420.86 (M+1)$^+$.

Step D

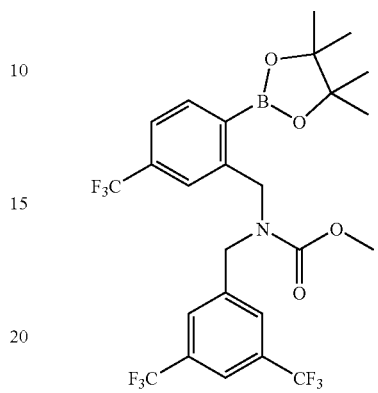

Methyl[3,5-bis(trifluoromethyl)benzyl][2-(4,4,5,5-tetramethyl-1,3,2-dioxaborolan-2-yl)-5-(trifluoromethyl)benzyl]carbamate Methyl[3,5-bis(trifluoromethyl)benzyl][2-iodo-5-(trifluoromethyl)benzyl]carbamate (218 mg, 0.373 mmol), potassium acetate (73.1 mg, 0.745 mmol), 1,1'-bis(diphenylphosphino) ferrocene-palladium dichloride dichloromethane adduct (60.8 mg, 0.075 mmol), bis(pinacolato) diboron (114 mg, 0.447 mmol) and 1,4-dioxane (1 ml) were sealed and subjected to microwave irradiation for a total of 35 minutes (15+20). TLC (20% EtOAc/hexanes, v/v) indicated the reaction was complete. Volatiles were removed under reduced pressure. The pot residue was worked up with brine, extracted with ethyl acetate, dried over Na$_2$SO$_4$, filtered and evaporated to afford a dark oil as a crude mixture containing the title compound, which was used without further purification for the next step. LCMS calc.=585.17; found=586.08 (M+1)$^+$.

Example 4A

Step E

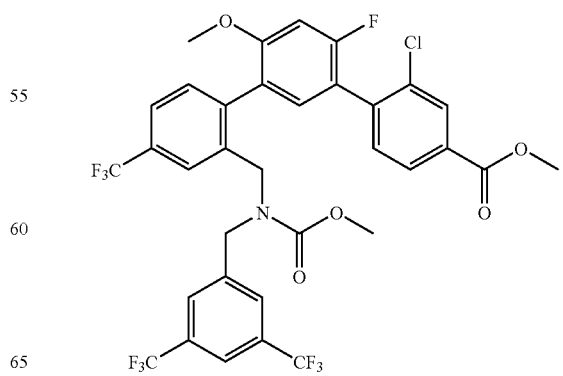

Methyl 2"-{[[3,5-bis(trifluoromethyl)benzyl](methoxycarbonyl)amino]methyl}-2-chloro-6'-fluoro-4'-methoxy-4"-(trifluoromethyl)-1,1':3',1"-terphenyl-4-carboxylate Methyl[3,5-bis(trifluoromethyl)benzyl][2-(4,4,5,5-tetramethyl-1,3,2-dioxaborolan-2-yl)-5-(trifluoromethyl)benzyl]carbamate (100 mg, 0.171 mmol), methyl 2-chloro-2'-fluoro-5'-iodo-4'-methoxybiphenyl-4-carboxylate (71.9 mg, 0.171 mmol), 1,1'-bis(diphenylphosphino) ferrocene-palladium dichloride dichloromethane adduct (13.95 mg, 0.017 mmol), potassium carbonate (0.256 ml, 0.513 mmol) and 1,4-dioxane (1 ml) were sealed and subjected to microwave irradiation for 30 min at 140° C. An aliquot indicated formation of the desired product. The crude reaction mixture was dried over $Na_2SO_4$. The resulting dark mixture was purified by preparative TLC (silica gel) developed by EtOAc/hexanes (20%, v/v) mixture to give a green glass as the title compound. LCMS calc.=751.12; found=752.36 $(M+1)^+$.

Example 4

Step F

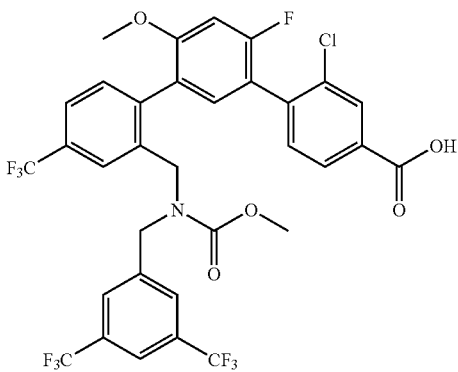

2"-{[[3,5-Bis(trifluoromethyl)benzyl](methoxycarbonyl)amino]methyl}-2-chloro-6'-fluoro-4'-methoxy-4"-(trifluoromethyl)-1,1':3'1"-terphenyl-4-carboxylic acid Methyl 2"-{[[3,5-bis(trifluoromethyl)benzyl](methoxycarbonyl)amino]methyl}-2-chloro-6'-fluoro-4'-methoxy-4"-(trifluoromethyl)-1,1':3', 1"-terphenyl-4-carboxylate (34.7 mg, 0.0486 mmol), lithium hydroxide monohydrate (10 mg, 0.238 mmol), water (0.4 mL) and 1,4-dioxane (1 mL) were stirred at room temperature for 5.5 hours to complete the reaction. Crude mixture was acidified by HCl (aq, 1N, 6 mL). The resulting mixture was worked up with brine and extracted with ethyl acetate. The combined extracts were back-washed with water. The resulting organic layer was dried over $Na_2SO_4$, filtered and evaporated in vacuo to afford a clear oil. The resulting oil was purified on $SiO_2$ to afford as a clear glass 2"-{[[3,5-bis(trifluoromethyl)benzyl](methoxycarbonyl) amino]methyl}-2-chloro-6'-fluoro-4'-methoxy-4"-(trifluoromethyl)-1,1':3',1"-terphenyl-4-carboxylic acid. LCMS calc.=699.17; found=700.29 $(M+1)^+$. $^1$H NMR (CDCl$_3$, 500 MHz) δ 8.01 (s, 1H), 7.95 (d, J=7.5 Hz, 1H), 7.72 (s, 1H), 7.58 (d, J=8.0 Hz, 1H), 7.55-7.46 (m, 1.5H), 7.43-7.34 (m, 2.5H), 7.32-7.25 (m, 1H), 7.07-7.5 (m, 1H), 4.62-4.22 (m, 4H), 3.77 (s, 3H), 3.73 (d, J=17 Hz, 3H), 3.32 (s, 3H).

What is claimed is:

1. A compound having Formula Ia, or a pharmaceutically acceptable salt thereof, wherein

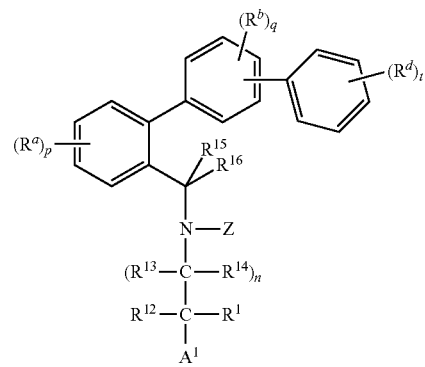

The phenyl ring of formula I that is substituted with $R^a$ groups may optionally have —N= in place of —(CH)= at one of the 4 positions that is open to substitution with $R^a$ in formula I;

$A^1$ is selected from the group consisting of:
  (a) an aromatic ring selected from phenyl and naphthyl;
  (b) a phenyl ring fused to a 5-7 membered non-aromatic cycloalkyl ring, which optionally comprises 1-2 double bonds;
  (c) a 5-6-membered heterocyclic ring having 1-4 heteroatoms independently selected from N, S, and O, and optionally also comprising 1-3 double bonds and a carbonyl group or —N(O)— group, wherein the point of attachment of $A^1$ to the carbon atom to which $A^1$ is attached is a carbon atom of $A^1$;
  (d) a benzoheterocyclic ring comprising a phenyl ring fused to a 5-6-membered heterocyclic ring having 1-3 heteroatoms independently selected from O, N, and S and optionally 1-2 double bonds, wherein the point of attachment of $A^1$ to the carbon atom to which $A^1$ is attached is a carbon atom of $A^1$; and
  (e) a —$C_3$-$C_8$ cycloalkyl ring optionally having 1-3 double bonds;

wherein $A^1$ is optionally substituted with 1-5 substituent groups independently selected from $R^c$;

Each $R^a$, $R^b$, and $R^c$ is independently selected from the group consisting of —$C_1$-$C_6$ alkyl, —$C_2$-$C_6$ alkenyl, —$C_2$-$C_6$ alkynyl, —$C_3$-$C_8$ cycloalkyl optionally having 1-3 double bonds, —$OC_1$-$C_6$alkyl, —$OC_2$-$C_6$ alkenyl, —$OC_2$-$C_6$ alkynyl, —$OC_3$-$C_8$ cycloalkyl optionally having 1-3 double bonds, —C(=O)$C_1$-$C_6$alkyl, —C(=O)$C_3$-$C_8$ cycloalkyl, —C(=O)H, —$CO_2$H, —$CO_2C_1$-$C_6$alkyl, —C(=O)$SC_1$-$C_6$alkyl, —OH, —$NR^3R^4$, —C(=O)$NR^3R^4$, —$NR^3$C(=O)$OC_1$-$C_6$ alkyl, —$NR^3$C(=O)$NR^3R^4$, —S(O)$_x C_1$-$C_6$ alkyl, —S(O)$_y NR^3R^4$, —$NR^3$S(O)$_y NR^3R^4$, halogen, —CN, —$NO_2$, and a 5-6-membered heterocyclic ring having 1-4 heteroatoms independently selected from N, S, and O, said heterocyclic ring optionally also comprising a carbonyl group and optionally also comprising 1-3 double bonds, wherein the point of attachment of said heterocyclic ring to the ring to which $R^a$, $R^b$, or $R^c$ is attached is a carbon atom, wherein said heterocyclic ring is optionally substituted with 1-5 substituent groups independently selected from halogen, —$C_1$-$C_3$ alkyl, and —OC$_1$-C$_3$ alkyl, wherein —C$_1$-C$_3$ alkyl and —OC$_1$-C$_3$ alkyl are optionally substituted with 1-7 halogens;

wherein when R$^a$, R$^b$, and R$^c$ are selected from the group consisting of —C$_1$-C$_6$ alkyl, —C$_2$-C$_6$ alkenyl, —C$_2$-C$_6$ alkynyl, —C$_3$-C$_8$ cycloalkyl optionally having 1-3 double bonds, —OC$_1$-C$_6$alkyl, —OC$_2$-C$_6$ alkenyl, —OC$_2$-C$_6$ alkynyl, —OC$_3$-C$_8$ cycloalkyl optionally having 1-3 double bonds, —C(=O)C$_1$-C$_6$alkyl, —C(=O)C$_3$-C$_8$ cycloalkyl, —CO$_2$C$_1$-C$_6$alkyl, —C(=O)SC$_1$-C$_6$alkyl, —NR$^3$C(=O)OC$_1$-C$_6$ alkyl, and —S(O)$_x$C$_1$-C$_6$ alkyl, then R$^a$, R$^b$, and R$^c$ are optionally substituted with 1-15 halogens and are optionally substituted with 1-3 substituent groups independently selected from (a) —OH, (b) —CN, (c) —NR$^3$R$^4$, (d) —C$_3$-C$_8$ cycloalkyl optionally having 1-3 double bonds and optionally substituted with 1-15 halogens, (e) —OC$_1$-C$_4$alkyl optionally substituted with 1-9 halogens and optionally substituted with 1-2 substituent groups independently selected from —OC$_1$-C$_2$ alkyl and phenyl, (f) —OC$_3$-C$_8$ cycloalkyl optionally having 1-3 double bonds and optionally substituted with 1-15 halogens, (g) —CO$_2$H, (h) —C(=O)CH$_3$, (i) —CO$_2$C$_1$-C$_4$alkyl which is optionally substituted with 1-9 halogens, and (j) phenyl which is optionally substituted with 1-3 groups independently selected from halogen, —CH$_3$, —CF$_3$, —OCH$_3$, and —OCF$_3$;

wherein 2 groups R$^a$ that are on adjacent carbon atoms of the phenyl or optional pyridinyl ring of Formula I may optionally be joined to form a bridging moiety selected from —CH$_2$CH$_2$CH$_2$—, —CH$_2$CH$_2$CH$_2$CH$_2$—, and —CH=CH—CH=CH—, thereby yielding a cyclopentyl, cyclohexyl, or phenyl ring fused to the phenyl ring or optional pyridinyl ring of Formula I, wherein said cyclopentyl, cyclohexyl, or phenyl ring that is fused to the phenyl or optional pyridinyl ring of Formula I is optionally substituted with 1-2 groups R$^a$, which cannot be joined together to form additional fused rings;

Each R$^d$ is independently selected from the group consisting of —C$_1$-C$_4$alkyl, —C$_2$-C$_4$ alkenyl, cyclopropyl, —OC$_1$-C$_4$alkyl, —C(=O)C$_1$-C$_4$alkyl, —C(=O)H, —CO$_2$H, —CO$_2$C$_1$-C$_4$alkyl, —OH, —NR$^3$R$^4$, —NR$^3$C(=O)OC$_1$-C$_4$alkyl, —S(O)$_x$C$_1$-C$_2$ alkyl, halogen, —CN, —NO$_2$, and a 5-6-membered heterocyclic ring having 1-2 heteroatoms independently selected from N, S, and O, wherein the point of attachment of said heterocyclic ring to the phenyl ring to which R$^d$ is attached is a carbon atom, wherein said heterocyclic ring is optionally substituted with 1-5 substituent groups independently selected from halogen;

wherein when R$^d$ is selected from the group consisting of —C$_1$-C$_4$ alkyl, —C2-C$_4$ alkenyl, cyclopropyl, —OC$_1$-C$_4$alkyl, —C(=O)C$_1$-C$_4$alkyl, —CO$_2$C$_1$-C$_4$alkyl, —NR$^3$C(=O)OC$_1$-C$_4$alkyl, and —S(O)$_x$C$_1$-C$_2$ alkyl, then the alkyl, alkenyl and cyclopropyl group of R$^d$ is optionally substituted with 1-5 halogens and is optionally substituted with one substituent group selected from (a) —OH, (b) —NR$^3$R$^4$, (c) —OCH$_3$ optionally substituted with 1-3 fluorine atoms and optionally substituted with one phenyl group, and (d) phenyl which is optionally substituted with 1-3 groups independently selected from halogen, —CH$_3$, —CF$_3$, —OCH$_3$, and —OCF$_3$;

n is 0 or 1;
p is an integer from 0-4;
q is an integer from 0-4;
t is an integer from 0-5;
x is 0, 1, or 2;
y is 1 or 2;

Z is selected from the group consisting of —S(O)$_x$C$_1$-C$_6$ alkyl, —S(O)$_2$NR$^{17}$R$^{18}$, —C(=S)OC$_1$-C$_6$alkyl, and —C(=O)X, wherein X is selected from the group consisting of H, —C$_1$-C$_6$ alkyl, —OC$_1$-C$_6$ alkyl, —SC$_1$-C$_6$ alkyl, and —NR$^3$ R$^4$; wherein —C$_1$-C$_6$ alkyl in all instances is optionally substituted with 1-13 halogens and 1-2 substituents independently selected from —OC$_1$-C$_3$alkyl, —CN, and —NO$_2$, wherein —OC$_1$-C$_3$alkyl is optionally substituted with 1-7 halogens and is optionally also substituted with 1-2 -OC$_1$-C$_2$ alkyl;

R$^1$, R$^{12}$, R$^{13}$, R$^{14}$, R$^{15}$, and R$^{16}$ are each independently selected from the group consisting of H, —OH, halogen, —C$_1$-C$_4$ alkyl, —C$_3$-C$_6$ cycloalkyl, —OC$_1$-C$_4$ alkyl, and —NR$^3$R$^4$, wherein —C$_1$-C$_4$ alkyl, —C$_3$-C$_6$ cycloalkyl, and —OC$_1$-C$_4$ alkyl are each optionally substituted with 1-9 halogens and are each optionally also substituted with 1-2 groups independently selected from —OH, —C(=O)CH$_3$, —OC(=O)CH$_3$, —OC$_1$-C$_2$ alkyl, and —OC$_1$-C$_2$ alkylene(OC$_1$-C$_2$alkyl), wherein either R$^1$ and R$^{12}$ together or R$^{13}$ and R$^{14}$ together may optionally form an oxo group;

R$^3$ and R$^4$ are each independently selected from H, —C$_1$-C$_5$ alkyl, —C(=O)C$_1$-C$_5$ alkyl and —S(O)$_y$C$_1$-C$_5$ alkyl, wherein —C$_1$-C$_5$ alkyl in all instances is optionally substituted with 1-11 halogens; and R$^{17}$ and R$^{18}$ are each independently selected from the group consisting of H, —C$_1$-C$_5$ alkyl, and —C$_3$-C$_7$ cycloalkyl, wherein —C$_1$-C$_5$ alkyl, and —C$_3$-C$_7$ cycloalkyl are optionally substituted with 1-13 halogens.

2. The compound of claim 1 having formula Ib, or a pharmaceutically acceptable salt thereof:

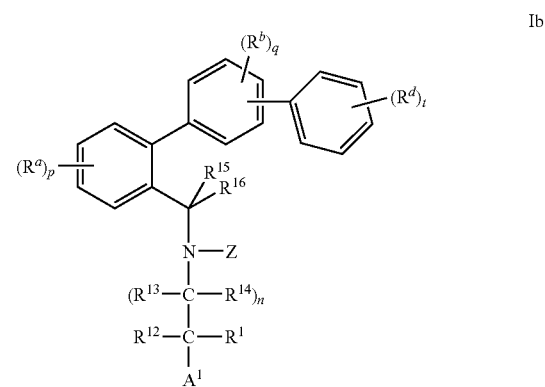

Wherein the phenyl ring of formula Ia that is substituted with R$^a$ groups may optionally have —N= in place of —(CH)= at one of the 4 positions that is open to substitution with R$^a$ in formula Ib; and other groups are as define in claim 1.

3. The compound of claim 1, or a pharmaceutically acceptable salt thereof, wherein the phenyl ring of formula Ia that is substituted with R$^a$ groups does not have the option of having —N= in place of —(CH)= at one of the 4 positions that is open to substitution with R$^a$ in formula Ia.

4. The compound of claim 3, or a pharmaceutically acceptable salt thereof wherein A$^1$ is selected from the group consisting of phenyl, naphthyl, —C$_3$-C$_6$ cycloalkyl, and a heterocyclic 5-6 membered ring having 1-3 heteroatoms independently selected from O, N, and S, and optionally also comprising 1-3 double bonds and a carbonyl group or —N(O)— group, wherein the point of attachment of $A^1$ to the carbon atom to which $A^1$ is attached is a carbon atom of $A^1$, wherein $A^1$ is optionally substituted with 1-2 substituent groups $R^c$, wherein each $R^c$ is independently selected from —$C_1$-$C_4$ alkyl, —$OC_1$-$C_3$ alkyl, —C(=O)$C_1$-$C_3$alkyl, —C(=O)H, —$NO_2$, —CN, —S(O)$_x$$C_1$-$C_3$ alkyl, —$NR^3R^4$, —$C_2$-$C_3$ alkenyl, —C(=O)$NR^3R^4$, halogen, —$C_3$-$C_6$ cycloalkyl, and a 5-6-membered heterocyclic ring having 1-3 heteroatoms independently selected from N, S, and O, and optionally also comprising 1-3 double bonds, wherein $C_1$-$C_3$ alkyl, $C_1$-$C_4$ alkyl, and $C_2$-$C_3$alkenyl in all instances are optionally substituted with 1-3 halogens, and —$C_3$-$C_6$ cycloalkyl and the 5-6-membered heterocyclic ring are optionally substituted with 1-3 substituents independently selected from halogen and —$C_1$-$C_3$ alkyl;

Each $R^a$ is independently selected from the group consisting of halogen, —$NR^3R^4$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —C(=O)$C_1$-$C_3$alkyl, —C(=O)$C_3$-$C_6$ cycloalkyl, —C(=O)H, —$CO_2$H, —$CO_2C_1$-$C_3$alkyl, —C(=O)$NR^3R^4$, —CN, —$NO_2$, and a 5-6-membered heterocyclic ring having 1-4 heteroatoms independently selected from N, S, and O, and optionally 1-3 double bonds, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$;

wherein 2 groups $R^a$ that are on adjacent carbon atoms of the phenyl ring of Formula Ia that is substituted with $R^a$ may optionally be joined to form a bridging moiety selected from —$CH_2CH_2CH_2$—, —$CH_2CH_2CH_2CH_2$—, and —CH=CH—CH=CH—, thereby yielding a cyclopentyl, cyclohexyl, or phenyl ring fused to the phenyl ring of Formula Ia, wherein said cyclopentyl, cyclohexyl, or phenyl ring of Formula Ia is optionally substituted with 1-2 groups $R^a$;

n is an integer selected from 0 and 1;
p and q are each integers independently selected from 0-3;
t when present is an integer selected from 0-4;
x is an integer selected from 0, 1, and 2;
y is an integer selected from 1 and 2;
$R^1$ is selected from the group consisting of H, F, OH, $C_1$-$C_3$ alkyl, and —$OC_1$-$C_3$ alkyl, wherein $C_1$-$C_3$ alkyl and —$OC_1$-$C_3$ alkyl are each optionally substituted with 1-3 halogens and also are optionally substituted with one —$OC_1$-$C_2$alkyl;
$R^3$ and $R^4$ are each independently selected from H and —$C_1$-$C_3$ alkyl;
$R^{12}$, $R^{13}$, $R^{14}$, $R^{15}$, and $R^{16}$ are each H or —$C_1$-$C_3$ alkyl; and
Z is selected from the group consisting of —C(=O)$C_1$-$C_3$ alkyl, —C(=O)O$C_1$-$C_3$ alkyl, —S(O)$_y$$C_1$-$C_3$ alkyl, —C(=O)H, —C(=O)$NR^3R^4$, —C(=O)S$C_1$-$C_3$ alkyl, and —C(=S)O$C_1$-$C_3$ alkyl.

5. The compound of claim 1, or a pharmaceutically acceptable salt thereof, wherein
$A^1$ is selected from the group consisting of phenyl, thienyl, furyl, pyridyl, 1-oxidopyridinyl, quinolyl, isoquinolyl, benzofuranyl, dihydrobenzofuranyl, indolyl, dihydroindolyl, oxazolyl, isoxazolyl, oxadiazolyl, and $C_3$-$C_6$ cycloalkyl;
$R^1$ is H or $CH_3$;
$R^{12}$, $R^{13}$, $R^{14}$, $R^{15}$, and $R^{16}$ are each H; and
n is 0.

6. The compound of claim 1, or a pharmaceutically acceptable salt thereof, wherein
$A^1$ is phenyl.

7. The compound of claim 1, or a pharmaceutically acceptable salt thereof, wherein $R^d$ is selected from the group consisting of halogen, —$C_1$-$C_3$ alkyl, —$C_2$-$C_3$ alkenyl, —$OC_1$-$C_3$ alkyl, —$NR^3R^4$, —$CO_2$H, —$CO_2C_1$-$C_3$ alkyl, and —CN, wherein —$C_1$-$C_3$ alkyl and —$C_2$-$C_3$ alkenyl in all uses are optionally substituted with 1-3 halogens and optionally one —OH group; and
t is an integer from 0-3.

8. The compound of claim 1, or a pharmaceutically acceptable salt thereof, wherein $R^a$, $R^b$ and $R^c$ are each independently selected from the group consisting of halogen, —$NR^3R^4$, —$C_1$-$C_3$ alkyl, —$OC_1$-$C_3$ alkyl, —$C_2$-$C_3$ alkenyl, —$C_3$-$C_6$ cycloalkyl optionally having a double bond, —$OC_3$-$C_6$ cycloalkyl optionally having a double bond, —C(=O)$C_1$-$C_3$alkyl, —C(=O)$C_3$-$C_6$ cycloalkyl, —C(=O)H, —$CO_2$H, —$CO_2C_1$-$C_3$alkyl, —C(=O)$NR^3R^4$, —CN, —$NO_2$, and a 5-6-membered heterocyclic ring having 1-4 heteroatoms independently selected from N, S, and O, and optionally 1-3 double bonds, wherein $C_1$-$C_3$ alkyl and —$C_2$-$C_3$ alkenyl in all instances are optionally substituted with 1-5 halogens, and —$C_3$-$C_6$ cycloalkyl and the 5-6-membered heterocyclic ring are in all occurrences optionally substituted with 1-3 substituents independently selected from halogen, —$C_1$-$C_3$ alkyl, —$OC_1$-$C_3$ alkyl, —$CF_3$, and —$OCF_3$.

9. The compound of claim 1, or a pharmaceutically acceptable salt thereof wherein $R^a$, $R^b$ and $R^c$ are each independently selected from the group consisting of halogen, cyclopropyl, —$NR^3R^4$, —$C_1$-$C_3$ alkyl, —$C_2$-$C_3$ alkenyl, —$OC_1$-$C_3$ alkyl, —CN, —$NO_2$, and pyridinyl, wherein cyclopropyl, $C_1$-$C_3$ alkyl and $C_2$-$C_3$ alkenyl in all instances are optionally substituted with 1-3 halogens, and pyridinyl is optionally substituted with 1-3 substituents independently selected from the group consisting of halogen, —$CH_3$, —$CF_3$, —$OCH_3$, and —$OCF_3$.

10. The compound of claim 1, wherein $R^a$, $R^b$ and $R^c$ are each independently selected from the group consisting of halogen, —$NR^3R^4$, —$C_1$-$C_3$ alkyl, —$C_2$-$C_3$ alkenyl, —$OC_1$-$C_3$ alkyl, —CN, —$NO_2$, and pyridinyl, wherein $C_1$-$C_3$ alkyl and $C_2$-$C_3$ alkenyl in all instances is optionally substituted with 1-3 halogens, and pyridinyl is optionally substituted with 1-3 substituents independently selected from the group consisting of halogen, —$CH_3$, —$CF_3$, —$OCH_3$, and —$OCF_3$, or a pharmaceutically acceptable salt thereof.

11. The compound of claim 2, or a pharmaceutically acceptable salt thereof,
wherein the phenyl ring of formula Ib that is substituted with $R^a$ groups does not have the option of having —N= in place of —(CH)= at one of the 4 positions that is open to substitution with $R^a$ in formula Ib;
$A^1$ is phenyl substituted with 1-2 substituent groups independently selected from $R^c$;
$R^a$, $R^b$, and $R^c$ are each independently selected from the group consisting of halogen, —$NR^3R^4$, —$C_1$-$C_3$ alkyl, —$C_2$-$C_3$ alkenyl, —$OC_1$-$C_3$ alkyl, —CN, and —$NO_2$, wherein $C_1$-$C_3$ alkyl and $C_2$-$C_3$ alkenyl in all instances is optionally substituted with 1-3 halogens;
$R^d$ is selected from the group consisting of halogen, —$C_1$-$C_3$ alkyl, —$C_2$-$C_3$ alkenyl, —$OC_1$-$C_3$ alkyl, —$NR^3R^4$, —CO₂H, —CO₂C₁-C₃ alkyl, and —CN, wherein —C₁-C₃ alkyl and —C₂-C₃ alkenyl in all uses are optionally substituted with 1-3 halogens;

Z is selected from the group consisting of —C(=O)C₁-C₃ alkyl, —C(=O)OC₁-C₃ alkyl, —S(O)$_y$C₁-C₃ alkyl, —C(=O)H, —C(=O)NR³R⁴, —C(=O)SC₁-C₃ alkyl, and —C(=S)OC₁-C₃ alkyl;

R¹, R¹², R¹⁵, and R¹⁶ are each H;

R³ and R⁴ are each independently selected from H and —C₁-C₃ alkyl;

p, q and t are integers independently selected from 0-2;

y is an integer selected from 1 and 2; and n is 0.

12. The compound of claim 11, or a pharmaceutically acceptable salt thereof, wherein R$^a$, R$^b$, and R$^c$ are each independently selected from the group consisting of halogen, —C₁-C₃ alkyl, —OC₁-C₃ alkyl, —CF₃, —OCF₃ —CN, and —NO₂;

R$^d$ is selected from the group consisting of halogen, —C₁-C₃ alkyl, —OC₁-C₃ alkyl, —CO₂H, —CO₂C₁-C₃ alkyl, —CF₃, —OCF₃ and —CN;

Z is selected from the group consisting of —C(=O)C₁-C₃ alkyl, —C(=O)OC₁-C₃ alkyl, —S(O)$_y$C₁-C₃ alkyl, —C(=O)H, and —C(=O)NR³R⁴;

R³ and R⁴ are each independently selected from H and —CH₃; and p, q and t are integers independently selected from 1-2.

13. A pharmaceutical composition comprising the compound of claim 1, or a pharmaceutically acceptable salt thereof, and a pharmaceutically acceptable carrier.

14. The compound of claim 12, or a pharmaceutically acceptable salt thereof shown below:

| Ex. | Structures |
|---|---|
| 1 | (structure) |
| 1A | (structure) |
| 2 | (structure) |
| 3 | (structure) |
| 4 | (structure) |
| 4A | (structure) |

15. A pharmaceutical composition comprising the compound of claim 1 or a pharmaceutically acceptable salt thereof, a pharmaceutically acceptable carrier, and one or more active ingredients selected from the group consisting of:
- (i) HMG-CoA reductase inhibitors;
- (ii) bile acid sequestrants;
- (iii) niacin and related compounds;
- (iv) PPARα agonists;
- (v) cholesterol absorption inhibitors;
- (vi) acyl CoA:cholesterol acyltransferase (ACAT) inhibitors;
- (vii) phenolic anti-oxidants;
- (viii) microsomal triglyceride transfer protein (MTP)/ApoB secretion inhibitors;
- (ix) anti-oxidant vitamins;
- (x) thyromimetics;
- (xi) LDL (low density lipoprotein) receptor inducers;
- (xii) platelet aggregation inhibitors;
- (xiii) vitamin B12 (also known as cyanocobalamin);
- (xiv) folic acid or a pharmaceutically acceptable salt or ester thereof;
- (xv) FXR and LXR ligands;
- (xvi) agents that enhance ABCA1 gene expression; and
- (xvii) ileal bile acid transporters.

16. A method of treating atherosclerosis in a patient in need of treatment comprising the administration of a therapeutically effective amount of the compound of claim 1 to said patient, or a pharmaceutically acceptable salt thereof.

17. A method of raising HDL-C in a patient in need of treatment comprising the administration of a therapeutically effective amount of the compound of claim 1 to said patient, or a pharmaceutically acceptable salt thereof.

* * * * *